United States Patent
Sellek-Prince

(10) Patent No.: US 7,300,804 B2
(45) Date of Patent: Nov. 27, 2007

(54) METHOD AND APPARATUS FOR CONTROLLING THE UNIFORM SMEARING OF A BIOLOGICAL LIQUID OVER A SUBSTRATE

(75) Inventor: Jose Sellek-Prince, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 421 days.

(21) Appl. No.: 10/989,172

(22) Filed: Nov. 15, 2004

(65) Prior Publication Data

US 2006/0105462 A1    May 18, 2006

(51) Int. Cl.
*G01N 33/555* (2006.01)
(52) U.S. Cl. .................. 436/520; 436/527; 436/164; 422/55
(58) Field of Classification Search .................. None
See application file for complete search history.

(56) References Cited

U.S. PATENT DOCUMENTS

| 5,209,903 A | 5/1993 | Kanamori et al. |
| 5,479,009 A | 12/1995 | Jablonski et al. |
| 5,537,203 A | 7/1996 | Carr |
| 5,650,332 A | 7/1997 | Gao et al. |
| 5,665,312 A | 9/1997 | Sperber et al. |
| 5,730,939 A * | 3/1998 | Kurumada et al. ........... 422/67 |

FOREIGN PATENT DOCUMENTS

| JP | 08094441 A * | 4/1996 |
| JP | 3662057 B2 * | 6/2005 |

\* cited by examiner

*Primary Examiner*—Yelena G. Gakh
(74) *Attorney, Agent, or Firm*—Warren W. Kurz; Mitchell E. Alter

(57) ABSTRACT

A method and apparatus for controlling the processing of a liquid sample, e.g., a blood sample, based on a measurement related to the sample's ability to coat a surface against which the sample is brought into contact while being routinely transported. Preferably, the sample is advanced through a tube, and the amount of sample residue remaining within the tube is measured and correlated to coating process subsequently carried out on the sample, e.g., a process for producing blood-smears on a microscope slide. In a preferred embodiment, the amount of sample residue in a blood-transport tube is used to control the motion profile (i.e., acceleration and velocity) of a drop-spreading member used to spread a blood drop on a microscope slide in an automated slide-making instrument.

20 Claims, 4 Drawing Sheets

| SAMPLE | WBC | HGB | HCT | MCV | MPV | RDW | PLT | PDW | GEN*S SM VELOCITY (IN/SEC) | GEN*S SM ACCELERATION (in²/sec) | RESIDUE SENSOR OUTPUT (V) | FIGURE 4 VELOCITY (in/sec) | FIG. 5 ACCELERATION (in²/sec) |
|---|---|---|---|---|---|---|---|---|---|---|---|---|---|
| 1 | 9.60 | 16.03 | 49.19 | 97.40 | 9.11 | 14.30 | 217 | 16.44 | 4.64 | 25.0 | 0.46 | 4.5 | 19.0 |
| 2 | 3.63 | 16.15 | 47.25 | 86.80 | 8.83 | 13.36 | 217 | 16.45 | 5.21 | 25.0 | 0.48 | 4.8 | 23.0 |
| 3 | 4.68 | 12.36 | 36.05 | 86.50 | 8.87 | 13.26 | 292 | 16.57 | 6.77 | 25.0 | 0.56 | 6.0 | 36.0 |
| 4 | 4.07 | 8.24 | 24.29 | 86.50 | 8.64 | 13.53 | 373 | 16.60 | 6.16 | 25.0 | 0.68 | 8.0 | 58.0 |
| 5 | 4.86 | 7.86 | 23.83 | 96.40 | 8.94 | 14.22 | 244 | 16.21 | 7.82 | 25.0 | 0.63 | 7.2 | 50.0 |
| 6 | 4.07 | 6.17 | 18.73 | 95.60 | 8.48 | 14.64 | 230 | 16.08 | 9.23 | 60.0 | 0.73 | 8.8 | 67.0 |
| 7 | 1.83 | 5.51 | 16.83 | 93.20 | 7.59 | 14.82 | 73 | 17.67 | 8.77 | 60.0 | 0.75 | 9.1 | 70.0 |

FIG. 6

METHOD AND APPARATUS FOR CONTROLLING THE UNIFORM SMEARING OF A BIOLOGICAL LIQUID OVER A SUBSTRATE

BACKGROUND OF THE INVENTION

1. Field of the Invention

The present invention relates to improvements in apparatus and methods for processing biological liquids, e.g., blood samples, based on measurements made during the transport of such liquids to a liquid-processing station. More particularly, it relates to improvements in apparatus and methods for adjusting a liquid-processing procedure, for example, a procedure for producing a blood-smear atop a microscope slide or the like, based on an "in-transit" measurement related to the coating characteristics of such liquids.

2. The Prior Art

In the analysis of whole blood samples, various automated flow-cytometric instruments (e.g., hematology and fluorescence flow cytometry instruments) are commonly used to differentiate and enumerate the various sub-populations of red and white blood cells comprising a unit volume of sample. Such instruments operate in a known manner to differentiate each of the sample cells by causing the cells to pass, one-at-a-time, through a cell-interrogation zone of the instrument. While passing through this zone, each cell is counted and "typed," typically through a combination of physical, electrical and/or optical measurements made substantially simultaneously on the cell. In the event the measured and calculated values provided by these clinical instruments are within "normal" limits, no further sample analysis is usually required, and the results are reported accordingly. However, in the event the sample analysis indicates an abnormality in the sample, either in terms of the number of cells of a particular sub-population, or in the level of a measured or calculated sample parameter, a visual inspection of the sample may be required to complete the analysis. Such an inspection is commonly effected by depositing a drop of sample on a microscope slide, and spreading or "smearing" the drop across the slide surface with a straight-edged smearing member (typically the edge of another microscope slide) to produce a "blood-smear" that can be manually analyzed under a microscope. Ideally, the blood-smears are of uniform length, and each comprises a monolayer of cells. In such a layer, all cells on the slide are visible under a microscope, with none obscuring another.

While blood-smears of the above type are often produced manually, they often vary dramatically in quality, depending on the skill of the technician. Thus, various automated slide-making instruments have been devised which take much of the "guess-work" out of the smear-producing process. One such slide-maker is the Model Gen*S™ Slidemaker, manufactured and sold by Beckman Coulter, Inc., Fullerton, Calif. Details of this instrument are described in the commonly assigned U.S. Pat. No. 5,650,332 issued in the names of Gao and Sperber. This particular slide-maker is actually an accessory instrument that is designed to be used with a "host" hematology instrument, i.e., the Model Gen*S™ Blood Analyzer, also made by Beckman Coulter, Inc. In addition to counting and differentiating red cells, white cells and platelets in the blood sample, the host instrument operates to measure or calculate several other blood sample characteristics, including the hematocrit (HCT) of the sample, the hemoglobin concentration (Hgb) of the sample's red blood cells, the red blood cell indices (RBCI), and the red cell distribution width (RDW). Based on the values of up to eight different sample parameters determined by the host instrument, the slide-making instrument acts to calculate (using a relatively complex algorithm containing such parameters) a "motion profile" that controls the acceleration and velocity of a drop-smearing member used to spread a blood drop atop the microscope slide in order to achieve a desired blood-smear thickness and length. The algorithms used by the Gen*S Slidemaker attempt to predict how blood components will interact with each other when the blood is smeared. As indicated above, the ideal thickness of the blood smear is that which provides a monolayer of cells, and a desired nominal smear length (e.g., about 1.4 inches for a standard microscope slide). While this approach to automated slide-making produces blood smears with relatively good precision and reproducibility, it will be appreciated that it does not lend itself to use in a stand-alone slide-maker in which a blood smear is to be made without a prior sample analysis by another instrument.

In U.S. Pat. No. 5,209,903 to Kanamori et al., another multi-instrument blood analysis system is disclosed. One component of such system is an "automatic blood smear-generator" that includes a relatively simple apparatus for measuring the "viscosity" of the blood sample being processed. Here, the viscosity information is used to control the smear-making process; in this case, it is used to control the size of the blood drop to be smeared, the angle of a smearing blade, and/or the velocity of the smearing blade. The viscosity measurement is made while a portion of the blood sample is being transported through tubing from a test tube containing the sample to a blood-drop-dispensing needle. Specifically, a syringe pump is used to aspirate the blood sample into the transport tubing. As the blood moves through the tubing, each of a pair of photo-sensors positioned at spaced locations along the tubing length produces a timing signal as the forward-most surface of the aspirated blood sample passes by. Since a more viscous (thicker) blood sample will flow at a slower rate through the tubing than a less viscous (thin) blood sample for a given syringe force, the elapsed time between the production of the two timing signals will indicate the viscosity of the blood sample. The longer the elapsed time between the timing signals, the higher the sample viscosity; and vice versa. A high viscosity determination operates to reduce the rate of movement of the smearing blade in order to achieve a desired blood smear thickness and length. Conversely, a low viscosity determination will cause the smearing blade to be advanced at a faster rate. While, this scheme of adjusting the blood-smearing process on the basis of a viscosity measurement may enhance the uniformity of blood smears for a some types of blood samples, it does not necessarily do so for a wide variety of blood samples. As may be appreciated, the speed at which a sample liquid can be made to pass through a tube is not necessarily indicative of how well such sample will coat a supporting substrate after being spread thereon. For example, a drop of mercury cannot be uniformly spread atop a substrate not matter what its viscosity or the speed of the smearing blade. The surface tension of liquid mercury is simply too great to allow such spreading. Similarly, attempting to smear a drop of liquid atop a highly polished or adhesive surface is likely to fail if the frictional forces between the liquid and the surface are too low. Thus, it will be appreciated that viscosity of a blood sample is only one of several factors at work in determining the quality of a blood smear.

An "idealized method" for achieving uniformity in the production of blood smears would be to perform two successive blood smears, i.e., a "test smear" followed by the "final smear." By measuring the smear length and/or the smear thickness of the test smear, the motion profile of the drop-spreading member can be adjusted to produce substantially uniform final smears. But, this approach would be problematic in that it is wasteful of blood, it requires the use of two slides, and it significantly reduces throughput of the slide-making instrument.

SUMMARY OF THE INVENTION

In view of the above discussion, an object of this invention is to provide an improved method and apparatus for automatically producing smears of a sample liquid atop a supporting substrate.

A more specific object of the invention is to provide an improved method and apparatus for controlling the movement of a blood drop-spreading member used in an automated slide-making instrument to produce blood-smears atop a supporting substrate, e.g., a planar surface of a microscope slide.

A further, and more general, object of this invention is to provide an improved method and apparatus for determining the ability of a liquid to be processed, e.g., to be coated on a substrate, based on a measurement made as the liquid is advanced to a liquid-processing station.

The present invention is based on the recognitions that (1) the process of advancing a blood sample through tubing, e.g., for the purpose of transferring a portion of a blood sample from a blood container to the tip of a drop-dispensing needle (or the like) used in an automated slide-making instrument to deposit a blood drop atop a slide, leaves behind a useful residue inside the tube, and (2) that this residue, when quantized, can be used to control the further processing of the blood, e.g., to control the motion profile of a blood-smearing member of an automated slide-making instrument used to produce blood smears from a variety of different blood samples. In effect, the blood residue in the tube serves as a "test" smear that can be used, e.g., to control the production of the "final smear" referred to in the above-noted "idealized method" for controlling smear uniformity in an automated slide maker. Of course, such quantized residue could be used to control any further processing of the sample for which the residue provides useful information regarding such processing.

Thus, according to one aspect of the invention, an improved method is provided for controlling the processing of a liquid sample based on its surface-coating characteristics. Such method comprises the steps of (a) advancing a volume of liquid sample through a tubular member, (b) detecting the volume of residue of the liquid sample remaining within the tubular member after such volume of sample has been advanced through the tubular member, and (c) controlling the subsequent processing of the liquid sample based on the amount of residue detected.

As indicated above, this general method of the invention has been found to be particularly useful in the production of sample smears of the type described. Thus, according to a second aspect of the invention, there is provided an improved method for controlling the motion profile (i.e., the acceleration and velocity) of a movably-mounted drop-spreading member in an automated slide-making instrument. Such method comprises the steps of (a) advancing a volume of sample through a tubular member, such volume containing a drop of sample to be spread by movement of the drop-spreading member, (b) detecting the amount of residue of the sample remaining within the tubular member after such volume of sample has been advanced through the tubular member, and (c) controlling the motion profile of the drop-spreading member to spread the drop of sample atop a drop-supporting surface on the basis of the amount of sample residue detected.

According to a third aspect of the invention, apparatus is provided for carrying-out the methods of the invention. A particularly preferred apparatus comprises (i) a light-integrating sphere positioned to enclose an optically transparent tube portion through which a liquid sample containing a sample drop to be processed is advanced, (ii) a light-transmitter for introducing into the interior of the integrating sphere light of a wavelength absorbed by the sample liquid, (iii) a light-sensor for sensing the intensity of light within the integrating sphere, and (iv) a logic and control unit operatively coupled to the light-sensor for producing a control signal representing the difference of the light intensity within the integrating sphere before and after the sample liquid has passed therethrough. Such control signal, which represents the amount of light-absorbing residue of sample remaining in the tube portion after the sample volume has completely passed through the tube portion, is used to control, for example, the motion profile of a drop-spreading member of a slide-making instrument.

By detecting the amount of residue of a sample that has passed through a tube as it advances, for example, towards a drop-dispensing position in a slide-making instrument, a control signal is provided which correlates well with the ability of the sample to be uniformly spread and thereby provide a coating atop a supporting substrate. Such a signal is significantly more accurate than the motion profile-controlling signals provided by the above-noted prior art techniques because it takes into account those characteristics of a liquid that are most important to the ability of a portion of a liquid drop to cling to its underlying substrate as the drop itself is advanced over the substrate. Important characteristics such as the surface tension in the liquid, the liquid's affinity for the underlying substrate, and the static and dynamic friction between the liquid and the substrate, are all lumped together and reflected in the residue-dependent control signal. In the case where the control signal is used to control the formation of a smear atop a substrate, it is preferred that the tube portion in which the sample residue is measured is fabricated from the same material as that from which the substrate (slide) is made. In such a case, the "two smears" of the above-noted "idealized method" are provided, one being made on a curvilinear surface, i.e., on the inside wall of the tube, and the other being made atop a planar surface. As a result of the invention, a significant improvement in the uniformity of smears produced by automated slide-making instruments is realized.

The invention and its advantages will be better appreciated from the ensuing description of preferred embodiments, reference being made to the accompanying drawings in which like reference characters denote like parts.

BRIEF DESCRIPTION OF THE DRAWINGS

FIG. 6 is a chart comparing the results of the motion profiles generated by a conventional slide-making instrument with the motion profiles generated by the apparatus of the present invention.

DETAILED DESCRIPTION OF PREFERRED EMBODIMENTS

As indicated above, the underlying discovery of the present invention is that the residue of a liquid clinging to a tubing's inside wall or any other surface that comes in contact with such liquid as it is transported, is substantially equivalent to making a test smear that is useful in the further processing of the liquid. Thus, for example, the way a blood sample behaves as it is spread onto a slide can be predicted by the way such blood sample spreads on and clings to other surfaces that come in contact with the blood sample before the slide is made. Consequently, by measuring the blood residue on such surfaces, a control signal can be produced which reflects the ability of the liquid to form a coating or "blood smear" on a slide. Such control signal can then be used to control, for example, the motion profile of the blood drop-spreading member of an automated slide maker. Alternatively, such signal may be correlated with other parameters of a liquid sample and used accordingly to control subsequent processing of the sample.

In the case of an automated slidemaker, the above-described discovery has particular utility in that an acceptable motion profile may be calculated from the residue measurement, without the need for creating a separate "test smear" of the type noted above. Additionally, as will be discussed hereinafter, a blood residue measurement provides a substantially more accurate motion profile for a drop-spreading member than the calculations performed in the above-noted slide-making instruments of the prior art.

Figure 1:
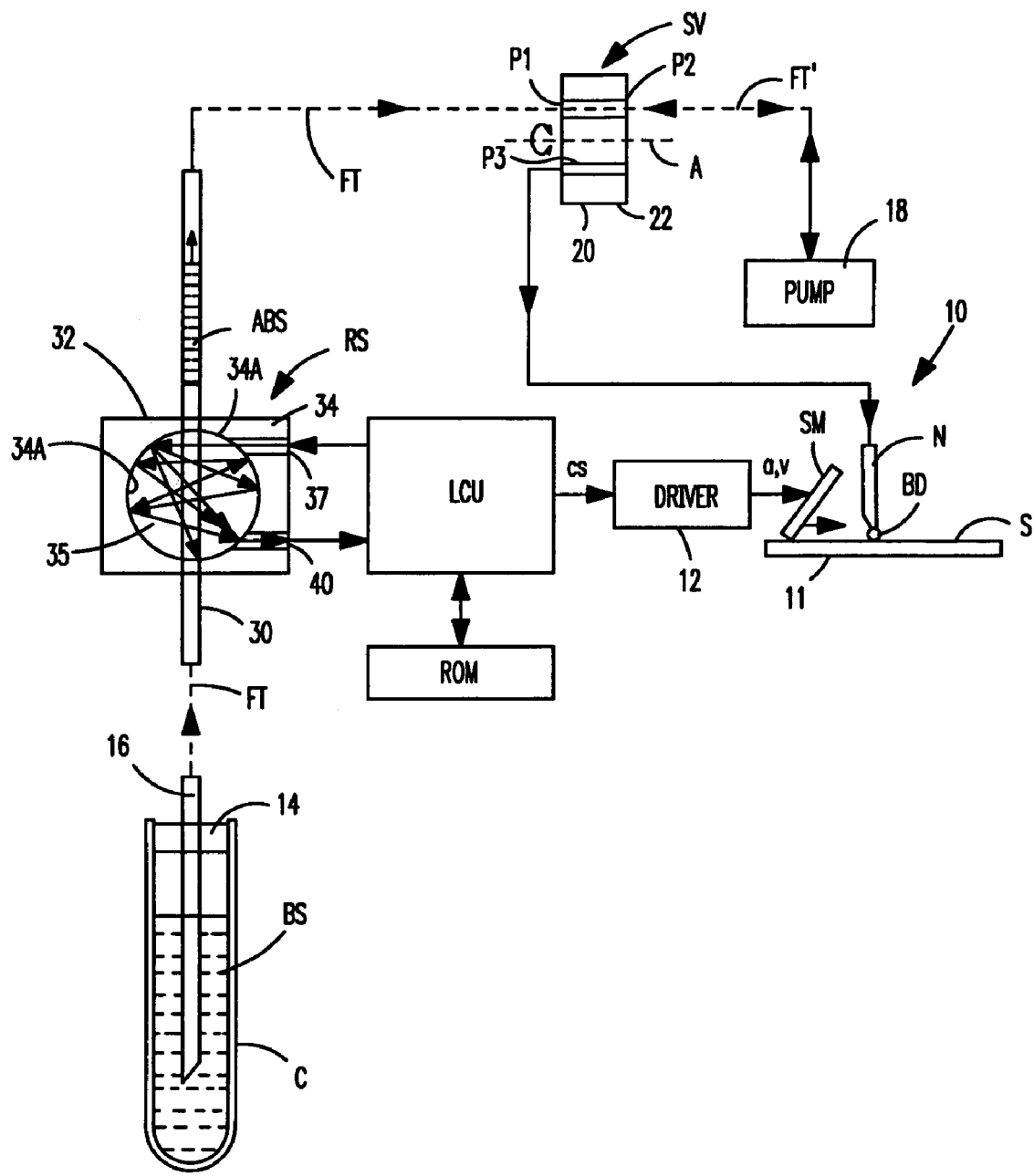
FIG. 1 is schematic illustration of a slide-making apparatus incorporating a preferred embodiment of the invention.

Still referring to FIG. 1, the blood sample BS for which a blood smear is to be made is initially contained by a test tube or container C having a puncturable seal 14 at its open end. A movably-mounted cannula 16 operates on command to puncture seal 14 to aspirate the sample in the container. A suction (negative) force is selectively applied to the cannula by a syringe pump 18 which serves to draw a predetermined volume of blood (including a drop to be smeared) from the container and into a flexible tube FT (schematically shown as a dashed line) connected to the cannula. This predetermined volume or "slug" of aspirated blood sample (ABS in the drawing) is drawn in its entirety through a pair of aligned ports P1, P2 formed in a pair of juxtaposed plates 20, 22 comprising a conventional shear valve SV. Having passed through the shear valve, the aspirated blood sample is temporarily stored in a second flexible tubing FT' connected between port P2 of the shear valve and the syringe pump P. Thereafter, valve plate 22 is rotated about axis A to align port P3, also formed in plate 20, with port P2 of valve plate 22, whereby the aspirated blood sample can now be advanced to the drop-dispensing needle N via a positive pressure applied by the syringe pump.

Now in accordance with one aspect of the present invention, apparatus is provided for detecting the amount of residue left behind by the aspirated blood sample ABS in a portion of the tubular conduit as it transported from the sample container C to the drop-dispensing needle N. As noted above, the amount of this residue directly correlates with the surface-coating characteristics of the aspirated blood sample ABS. By determining the amount of this residue before a blood smear is made atop substrate S, the blood-smearing process can be controlled to produce uniform blood smears for a wide variety of blood samples. In accordance with a preferred embodiment, such apparatus comprises a residue sensor RS (described below) and an optically transparent tubular member 30 connected in-line with flexible tubing FT, preferably between the aspirating cannula 16 and the shear valve SV. Preferably, the tubular member has the same inside diameter (between about 0.015 and 0.025 inches) as the flexible tubing FT, but it is made of the same material as substrate S, typically a glass material. However, as will be appreciated from the description below, the substrate and tubular member may be made of different materials, so long as they are similar in those characteristics which affect the ability of the sample to form a coating on the substrate. For example, the tubular member may be made of a transparent, medical grade polyvinyl chloride (PVC) material while the substrate is made of glass. In such a case, the flexible tubing FT and tubular member 30 can formed from a continuous piece of such transparent tubing. Thus, in operation, the aspirated blood sample ABS drawn from the container C will pass through tubular member 30 as it travels towards the shear valve SV. As it passes through tubular member 30, a portion of the aspirated blood sample will smear upon the interior wall of member 30 and thereby leave behind a detectable residue of blood within the tubular member. The amount of this residue has been found to correlate well with those characteristics of the whole blood which affect its ability to form a blood smear on the substrate S.

While various schemes (e.g., optical, ultrasonic, volumetric measurement schemes) may be employed to detect the amount of blood residue in tubular member 30 resulting from the passage of a blood sample therethrough, a particularly preferred residue sensor RS comprises a so-called "light-integrating sphere" 32 (shown in FIG. 1). Such a device is preferred because it is adapted to operate "in-line" with the sample-transport tubing FT, and because of its inherent ability to differentiate small differences in blood residues. A light-integrating sphere of the type preferred is commercially available from Labsphere, Inc., North Sutton, N.H. The technical details of such a device are disclosed, e.g., in U.S. Pat. No. 5,537,203, the contents of which are incorporated herein by reference.

As illustrated in FIG. 1, the light-integrating sphere 32 generally includes a housing 34 that defines a substantially spherically-shaped internal chamber 35. For the type of measurement made in accordance with the present invention, it is preferred that the diameter of chamber 35 is between about 15 and 30 mm. The chamber-defining wall 34A of housing 34 is coated with a highly reflective, but light-diffusing material that serves to distribute light, introduced into the chamber from an external source, uniformly throughout the chamber interior. Owing to the coating-characteristics of wall 34A, a light beam incident on such wall will undergo multiple diffused reflections. With each of these multiple diffused reflections, the internal sphere surface of chamber 35 acts as an array of infinitesimally small and uniform virtual light sources; hence, the averaging or integrating property of the integrating sphere 32. As a consequence of the high reflectivity property of the chamber's wall, a photon of light entering the chamber 35 will Referring now to FIG. 1, there is schematically illustrated a slide-making system 10 for producing a blood smears atop a planar substrate S; typically substrate S is one of the two opposing planar faces of a conventional microscope slide 11. Apparatus 10 comprises a movably-mounted drop-spreading member SM which is selectively driven in a linear direction, from left to right in the drawing (as indicated by the arrow) atop the planar substrate S. As disclosed in the above-mentioned U.S. Pat. No. 5,650,332, the details of which are incorporated herein by reference, the drop-spreading member SM may itself be a glass microscope slide which is positioned such that a linear edge thereof rests atop the planar substrate S, with the body of the drop-spreading member extending at an angle relative to the substrate S. Apparatus 10 further comprises a drop-dispensing needle N that serves to dispense, in a known manner, a blood drop BD of precise volume atop surface S. A driving mechanism 12, operatively connected to the drop-smearing member, operates on command from a suitably programmed logic and control unit LCU to slowly move the drop-spreading member (in the direction of the arrow) into contact with a blood drop atop substrate S. After a brief pause to enable the drop to wick towards each side of the spreading member, the spreading member is accelerated in the opposite direction (from right to left, in the drawing) at a predetermined rate until it reaches a desired velocity, at which time the spreading member maintains such velocity until the blood smear is completed. As member SM moves from right to left, the blood drop is spread in the same direction, thereby producing the desired blood smear on substrate S. Ideally, as noted above, all blood smears are of uniform length (e.g., 1.4 inches) and uniform thickness (preferably a monolayer of cells). Such uniformity is required, e.g., by automated optical apparatus that serves to subsequently analyze the blood smear so made. The acceleration and velocity (i.e., the "motion profile") of the drop-spreading member must be precisely controlled to account for variations in the blood sample that affect its ability to be spread in a way to achieve the desired uniformity in the blood smears. Various properties of the blood sample, including viscosity, surface tension, friction, and affinity for the substrate, affect the formation of a blood smear and, ideally, all such properties should be accounted for in determining the motion profile of the drop-spreading member. survive many reflections before being absorbed and dissipated as heat. When another photon enters the chamber 35 before the first one dissipates, the energy associated with it adds to that of other photons in a complex manner. This process continues until a balance is reached between incoming photons and absorbed photons—at which time a steady-state is reached. Time constants in the order of tens of nanoseconds are typical to reach this steady state. This process gives rise to a "sphere multiplier" factor. It can be shown that at any time after the steady-state light level has been reached, the energy contained within the integrating sphere is greater, by the sphere multiplier factor, than the energy content of the input flux. Due to this sphere multiplier factor, a small percentage drop in the sphere's average internal reflection, e.g., caused by the blood residue within member 30, results in a relatively large change in the output flux detected by the light detector 40. This change in light level can be detected and used to characterize the light-absorbing property of the object. Thus, by positioning tubular member 30 within chamber 35, the amount of light absorbed by the tubular member (and its contents) can be quantized. By selecting a tubular member that is transparent to the light introduced into the chamber, then any change in light level within the chamber can be attributed to the tube contents alone. Assuming the tube contents is a blood residue, the wavelength of the light used to illuminate the chamber should be that which is highly absorbed by the blood sample. Preferred wavelengths are about 465 nm. (blue light) and 520 nm. (green light), either of which wavelengths can be emitted by a suitable light-emitting diode (LED). A particularly preferred LED is the Nichia NSPB500S, which emits at a power level of about 6 milliwatts and at a wavelength of 465 nm.

Figure 2:
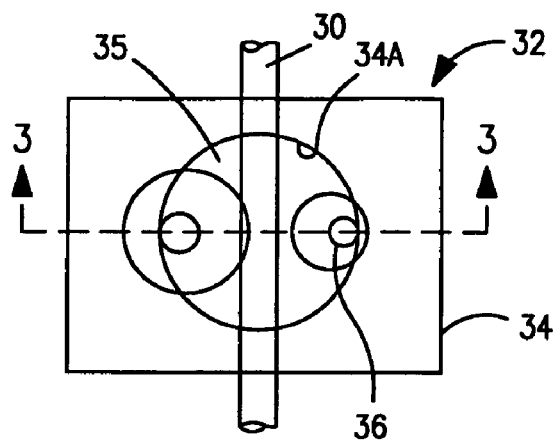
FIG. 2 is a cross-sectional illustration view of a preferred residue detector taken along the section line 2-2 shown in FIG. 3.
Figure 3:
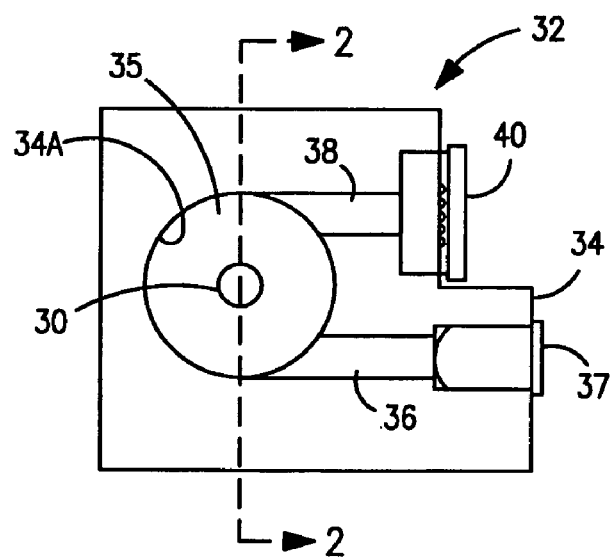
FIG. 3 is a cross-sectional illustration of the preferred residue detector shown in FIG. 2, taken along the section line 3-3.

Referring to the cross-sectional views of FIGS. 2 and 3, the light-integrating sphere 32 of FIG. 1 is shown in more detail. As shown, the tubular member 30 is inserted through a suitable opening formed in housing 34 to locate member 30 along a diameter of the spherical chamber 35. Housing 34 further defines a light-input channel 36 through which light emitted by a light source 37 (e.g., an LED of the above type) mounted on housing 34 can enter the spherical chamber. Housing 34 further defines an output channel 38 through which light that has entered the integrating sphere and has undergone multiple reflections therein can exit and thereby be measured by a photo-detector 40. A suitable photo-detector is a blue enhanced photodiode (e.g., the UDT Sensors Inc. PIN-5DP/SB, TO-5 package). Preferably, this photodiode is used in a photovoltaic mode for increased sensitivity. As will be obvious to those skilled in the art, many possible light source and detector arrangements may be used with the optical integrating sphere 32. Further, the word "light" as used herein is used in its ordinary sense as referring not only to visible electromagnetic radiation, but also to near-visible radiation, such as ultraviolet and infrared radiation.

In operation, the light detector 40 generates as an output an analog voltage signal which increases inversely with the amount of blood residue within tubular member 30, i.e., the output of the detector 40 will be highest when no blood residue remains in the member 30, and it will gradually decline as the residue increases. Thus, the amplitude of this output voltage signal is a quantification of the amount of residue in member 30 and it reflects the ability of the blood sample to coat the inner wall of member 30. The lower the output voltage, the greater the residue (coating) within member 30. This output voltage signal is provided to an analog-to-digital converter (ADC) 50 of the LCU which converts the analog output of the detector to a digital signal representing a digitized version of the residue measurement. This digitized signal is further processed by the LCU to generate a control signal CS that is applied to driver 12 to control the acceleration a and velocity v (i.e., the motion profile) of the drop-spreading member SM. In this application, a mathematical algorithm providing the relationship between the digitized output voltage (residue measurement) of the light detector 40 and the motion profile for the slidemaker is stored in a conventional read-only memory (ROM) of the LCU.

In another application of the residue sensor 32, instead of a motion profile being calculated by the LCU, the voltage signal is merely used as and displayed as a measurement of the coating characteristic of the blood sample. It is contemplated that such a blood parameter can be used to augment the blood sample parameters described in the Background section.

Figure 4:
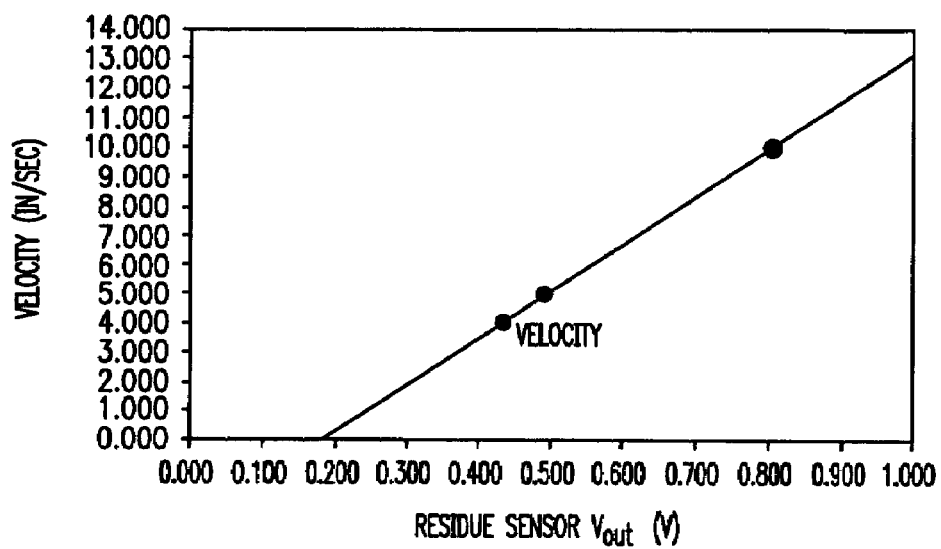
FIG. 4 is a graph illustrating the relationship between the output of a blood residue detector and a desired velocity for a drop-spreading member used to produce a blood smear from a drop of blood.
Figure 5:
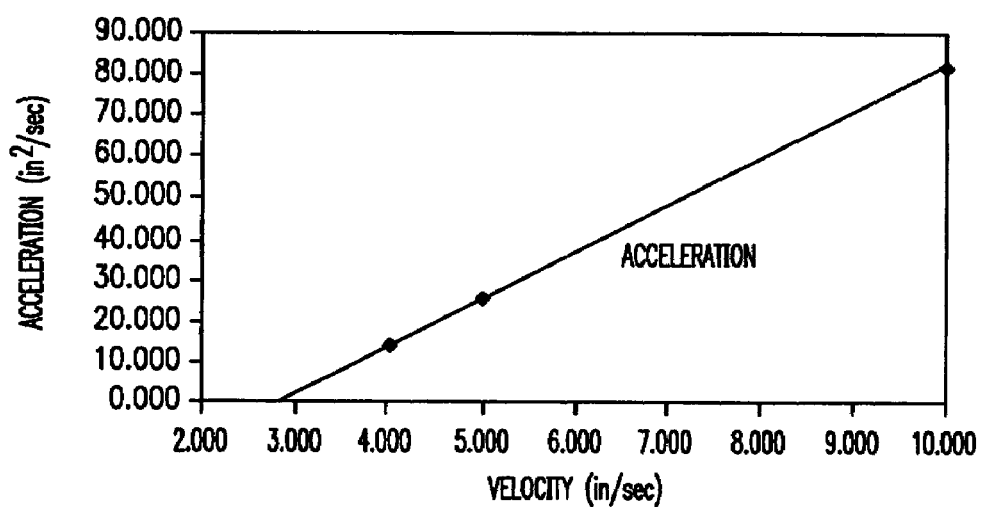
FIG. 5 is a graph illustrating the relationship between the velocity of a drop-spreading member and the desired initial acceleration of such member.

A preferred method will now be described for calculating the algorithm for the motion profile in the slidemaker application of the invention described above. This methodology has three stages. First, the residue sensor RS was characterized by first running in a conventional Gen*S Slidemaker (described above) three whole blood samples: a first sample having a high HCT value, a second sample having a medium HCT value, and a third sample having a low HCT values. The smear velocity and acceleration were manually adjusted by an operator so as to create a desired 1.400 inch long smear for each of these samples. A balance between velocity and acceleration was obtained by trial and error. These new velocity and acceleration values (the respective motion profiles) were recorded. Next, the voltage outputs of the residue sensor RS for the same three samples was obtained and recorded. In FIG. 4, the three voltage outputs of the residue sensor 32 are plotted on the x-axis and the manually-obtained velocity values from the Gen*S slidemaker are plotted on the y-axis. The result is that FIG. 4 is a residue sensor velocity curve relative to voltage output defined by the linear equation: y=16.0x−2.9. Likewise, in FIG. 5, the three velocity values are plotted on the x-axis and the manually obtained acceleration values from the Gen*S slidemaker are plotted on the y-axis. The result is that FIG. 5 is a residue sensor acceleration curve relative to velocity defined by the linear equation: y=11.0x−30.00. These values will hold true for all sensors of similar mechanical and optical characteristics.

Second, referring to FIG. 1, the syringe pump 19 is used to fill the tubular member 30 with a reference fluid, such as Isoton®, by aspirating the reference fluid from a container (not shown) containing such reference fluid. With the reference fluid in the member 30, the voltage from the residue sensor 32 is normalized to 1, either in hardware or software. The reference fluid is selected so that it does not absorb energy at the selected wavelength of the light from the light source 37; thus it will have a negligible effect on the sphere multiplier factor. Then, the reference fluid is removed by the syringe pump 18, and a segment of blood chased by air is moved through the tubular member 30. It is, of course, important that the segment of blood completely exits the chamber 35 of the integrating sphere 32; otherwise, the output of detector 40 will not be entirely a residue reading. The residue remaining on the inside wall of the tube 30 absorbs light in the spherical chamber 35 and reduces the integrating sphere's overall reflectivity. This in turn causes a change in the sphere multiplier and thereby reduces the detected flux measured by the light detector 40 as compared to the detected flux for the previously described Isoton measurement. As shown in FIG. 6, seven blood samples (column labeled "SAMPLE") ranging from high to low HCT ($4^{th}$ column in FIG. 6) were processed in this manner by the residue sensor RS. For each sample, the integrating sphere 32 generated both a residue voltage output (column labeled "RESIDUE SENSOR OUTPUT") from which a motion profile can be computed from the curves shown in FIGS. 4 and 5.

Third, as shown in FIG. 6, the accuracy of the motion profiles generated by the residue-sensor RS of FIG. 1 were compared to the accuracy of the motions profiles generated by the Gen*S slidemaker. Two consecutive blood smears for each of the seven samples where generated using a Gen*S slidemaker. The first smear of each sample was generated on the basis of the acceleration and velocity values calculated by the Gen*S slidemaker ("Gen*S SM VELOCITY" and "Gen*S ACCELERATION"). The second smear of each sample was generated on the basis of the acceleration and velocity values determined by the curves shown in FIGS. 4 and 5 (columns "FIG. 4 VELOCITY" and "FIG. 5 ACCELERATION"). Those slide smears whose motion profiles were adjusted based on measurements from the residue-sensor RS were more consistent in length than the Gen*S-adjusted smears. Furthermore, the Gen*S-based smears had a bias towards longer smears for lower HCT samples. This can be problematic if the blood sample also has low white blood cell count, as the cells tend to be widely spread in the longer smear, making it more difficult to find the white cells. Thus, the residue-sensor RS is a viable and preferred alternative to using the motion profiles generated by the Gen*S slidemaker.

Generally, it is desirable to determine the algorithms of FIGS. 4 and 5 for each residue-sensor made by the manufacturer, since variations are possible from sensor to sensor. Moreover, from time to time, the user of the residue sensor should repeat the methodology of creating FIGS. 4 and 5 (recompute the equations) to determine if there are sufficient changes in the equations, due to drift, to justify an update in the memory of the processing means (ROM), or an update the curves used, in the case of manually looking up a motion profile for the automatic slidemaker). It should be noted that, although glass capillary tubes (as tubular member 30) produce linear equations, such as those shown in FIGS. 4 and 5, the use of plastic capillary tubes tend to create non-linear equations. Although use of plastic capillary tubes and tubes made of yet other suitable materials are well within the scope of the present invention, glass for the capillary tubes (e.g., BK7 glass) is the preferred material, especially when slide 11 is made of glass.

As mentioned previously, methods of measuring the blood residue may include, but are not limited to, optical, ultrasonic or volumetric detectors. In the preferred embodiment of the present invention, the integrating sphere 32 was selected, based upon it having the sensitivity required to differentiate between small differences in blood residues. Another optical measurement scheme would be to take the capillary tube 30 with the residue therein, flush the tube out with predetermined amount of clear diluent, and then collect the resulting dilution. Then the coloration of the collected liquid (blood derivative, i.e., diluted blood) can be measured using conventional calorimetric measuring devices. This calorimetric measurement of the diluted blood will correlate to the blood residue in the tube.

The invention has been described in detail with particular reference to preferred embodiments thereof, but it will be understood that variations and modifications can be made without departing from the spirit of the invention, and such variations and modifications are intended to fall within the scope of the appended claims.

What is claimed is:

1. A method for controlling the application of a coating of a liquid sample on a substrate based on the surface-coating characteristics of said liquid sample for said substrate, said method comprising the steps of
   (a) advancing a volume of liquid sample completely through an open-ended tubular member, said tubular member having coating retention characteristics at least similar to those of said substrate;
   (b) determining the amount of a residue of the liquid sample remaining on the interior walls of said tubular member after such volume of the liquid sample has been advanced completely through the tubular member;
   (c) determining from said amount of residue the surface-coating characteristics of the liquid sample specific for the coating-retention characteristics of said tubular member and said substrate; and
   (d) controlling subsequent coating of said liquid sample on the substrate based on the determined surface-coating characteristics of said liquid sample for said substrate.

2. The method as defined by claim 1 wherein the amount of said residue is optically detected.

3. The method as defined by claim 2 wherein said amount of residue is directly detected optically by irradiating said tubular member with electromagnetic radiation of a wavelength substantially absorbed by said liquid sample, said tubular member being substantially transparent to said radiation, and detecting the respective levels of radiation absorbed by said tubular member with and without a liquid residue present therein.

4. The method as defined by claim 3 wherein said tubular member is positioned within a light-integrating sphere in which said radiation can be introduced and detected.

5. The method as defined by claim 3 wherein said tubular member is cleansed with a liquid that is substantially transparent to said radiation prior to said step of detecting said respective levels of radiation absorbed by said tubular member.

6. A method for controlling the motion profile of a movably-mounted drop-spreading member used in an automated slide-making instrument to spread a drop of a biological liquid sample atop a substrate, said method comprising the steps of;
   (a) advancing a volume of sample liquid completely through an open-ended tubular member, such volume containing a drop of biological liquid sample to be spread by movement of the drop-spreading member atop said substrate, said tubular member having coating retention characteristics at least similar to those of said substrate;
   (b) determining the amount of a residue of the liquid sample remaining on the interior walls of said tubular member after such volume of the liquid sample has been advanced completely through the tubular member;
   (c) determining from said amount of residue the surface-coating characteristics of the liquid sample specific for the coating-retention characteristics of said tubular member and said substrate, and;
   (d) controlling the motion profile of the drop-spreading member to spread the drop of biological liquid sample atop said substrate based on the determined surface-coating characteristics of said biological liquid sample for said substrate.

7. The method as defined by claim 6 wherein said biological liquid sample comprises a blood sample.

8. The method as defined by claim 7 wherein the residue of said blood sample is optically detected.

9. The method as defined by claim 8 wherein said optical detection step is effected by irradiating said tubular member with electromagnetic radiation of a wavelength substantially absorbed by said blood sample, said tubular member being substantially transparent to said radiation, and detecting the respective levels of radiation absorbed by said tubular member with and without a residue of blood sample therein.

10. The method as defined by claim 9 wherein said tubular member is positioned within a light-integrating sphere in which said radiation can be introduced and detected.

11. The method as defined by claim 9 wherein said tubular member is cleansed with a liquid that is substantially transparent to said radiation prior to said step of detecting said respective levels of radiation absorbed by said tubular member.

12. Apparatus for controlling the application of a coating of a liquid sample on a substrate based on the surface-coating characteristics of said liquid sample for said substrate, said apparatus comprising:
   (a) a pump for advancing a volume of liquid sample completely through an open-ended tubular member, said tubular member having coating-retention characteristics at least similar to those of said substrate;
   (b) a detector for detecting the amount of a residue of the liquid sample remaining on the walls of the tubular member after such volume of sample has been advanced completely through the tubular member; and
   (c) a controller for (a) determining from said amount of said residue the surface-coating characteristics of said liquid sample vis-à-vis the coating-retention of said tubular member and said substrate, and (b) for controlling the subsequent coating of said liquid sample on said substrate based on the detennined surface-coating characteristics of said liquid sample for said substrate [controlling the subsequent processing of the liquid sample based on the residue detected by said detector].

13. The apparatus as defined by claim 12 wherein said detector comprises (i) a light-integrating sphere positioned to enclose an optically transparent portion of said tubular member through which said liquid sample containing a sample drop to be coated is advanced, (ii) a light-transmitter for introducing into the interior of said integrating spheie radiation of a wavelength absorbed by the sample liquid, (iii) a light-sensor for sensing the intensity of light within the integrating sphere, and (iv) a logic and control unit operatively coupled to said light-sensor for producing a control signal representing the difference of the light intensity within said light-integrating sphere before and after said sample liquid has passed completely therethrough.

14. Apparatus for controlling the movement of a drop-spreading member in an automated slide-making instrument of the type in which a drop of a biological liquid sample is spread upon a substrate to produce a sample-smear adapted to be visually analyzed, said apparatus comprising:
   (a) a pump for advancing a volume of sample liquid completely through an open-ended tubular member, said volume containing a drop of sample liquid to be spread by movement of said drop-spreading member, and said tubular member having coating-retention characteristics at least similar to those of said substrate;
   (b) a detector for detecting the amount of residue of the sample remaining said tubular member after said volume of sample has been advanced completely through said tubular member; and
   (c) a logic and control unit, operatively coupled to said detector, for controlling the movement of said drop-spreading member to spread said drop of sample atop a drop-supporting surface on the basis on the amount of sample residue detected.

15. The apparatus as defined by claim 14 wherein said sample liquid comprises a blood sample.

16. The apparatus as defined by claim 15 wherein the residue of said blood sample is optically detected.

17. The apparatus as defined by claim 15 wherein said detector comprises a source of electromagnetic radiation for irradiating said tubular member with electromagnetic radiation of a wavelength substantially absorbed by said blood sample, said tubular member being substantially transparent to said radiation, and a radiation sensor for detecting the respective levels of radiation absorbed by said tubular member with and without a residue of blood sample therein.

18. The apparatus as defined by claim 17 wherein said tubular member is positioned within a light-integrating sphere in which said radiation can be introduced and sensed.

19. The apparatus as defined by claim 17 wherein said tubular member is cleansed with a liquid that is substantially transparent to said radiation prior to detecting said respective levels of radiation absorbed by said tubular member.

20. The apparatus as defined by claim 17 wherein said electromagnetic radiation is blue or green optical radiation.

* * * * *